United States Patent
Tornier et al.

(10) Patent No.: US 9,119,637 B2
(45) Date of Patent: Sep. 1, 2015

(54) ARTICULATED DRILL AND DEVICE FOR DRIVING IT IN A RECIPROCATING MOVEMENT

(71) Applicant: CLARIANCE, Dainville (FR)

(72) Inventors: Alain Tornier, Saint Ismier (FR); Guy Viart, Saint Leger (FR); Jean Yves Leroy, Campagne-les-Hesdin (FR); Brice Krier, Dainville (FR); Adrien Billon, Rochin (FR)

(73) Assignee: CLARIANCE, Dainville (FR)

( * ) Notice: Subject to any disclaimer, the term of this patent is extended or adjusted under 35 U.S.C. 154(b) by 279 days.

(21) Appl. No.: 13/687,226

(22) Filed: Nov. 28, 2012

(65) Prior Publication Data

US 2013/0138107 A1 May 30, 2013

Related U.S. Application Data

(60) Provisional application No. 61/564,412, filed on Nov. 29, 2011.

(51) Int. Cl.
A61B 17/16 (2006.01)

(52) U.S. Cl.
CPC .............. *A61B 17/16* (2013.01); *A61B 17/1631* (2013.01); *A61B 17/1642* (2013.01); *A61B 17/1671* (2013.01); *A61B 17/162* (2013.01)

(58) Field of Classification Search
CPC .................................................... A61B 17/1642
USPC ..................................................... 606/80, 170
See application file for complete search history.

(56) References Cited

U.S. PATENT DOCUMENTS

| | | | |
|---|---|---|---|
| 6,447,518 B1 * | 9/2002 | Krause et al. | 606/80 |
| 7,105,003 B2 * | 9/2006 | Hiltebrandt | 606/159 |
| 8,801,716 B2 * | 8/2014 | Meridew | 606/86 R |

FOREIGN PATENT DOCUMENTS

FR          11 00199          9/1955

* cited by examiner

*Primary Examiner* — Andrew Yang
(74) *Attorney, Agent, or Firm* — Young & Thompson

(57) ABSTRACT

The drilling device is composed of an articulated drill (1) provided with a metal tube (10) including, along its longitudinal axis XX', and at one of its ends, fixing elements (11) that cooperate with a device (2) for driving it in an oscillatory movement, while the other end includes a profile (12) with a succession of alternately concave and convex loops (13) ensuring the deformation of the profile along a radius of curvature r, and at least one series of teeth (15, 16) with cutting edges (17, 18).

4 Claims, 10 Drawing Sheets

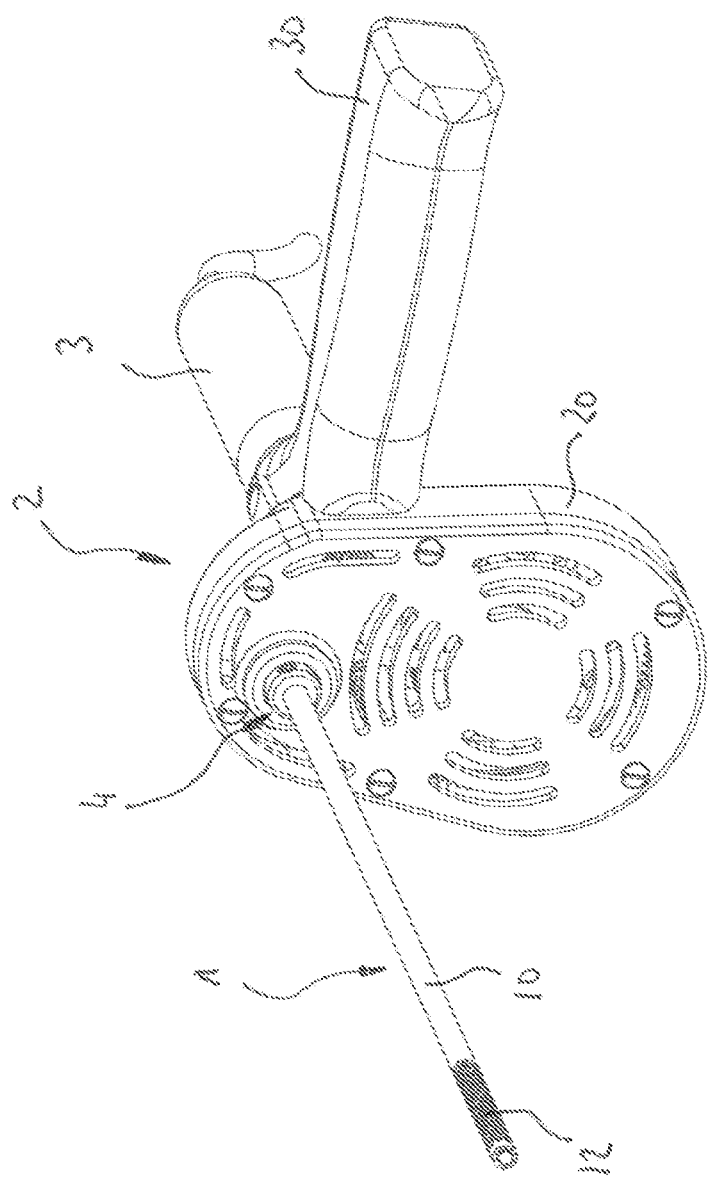

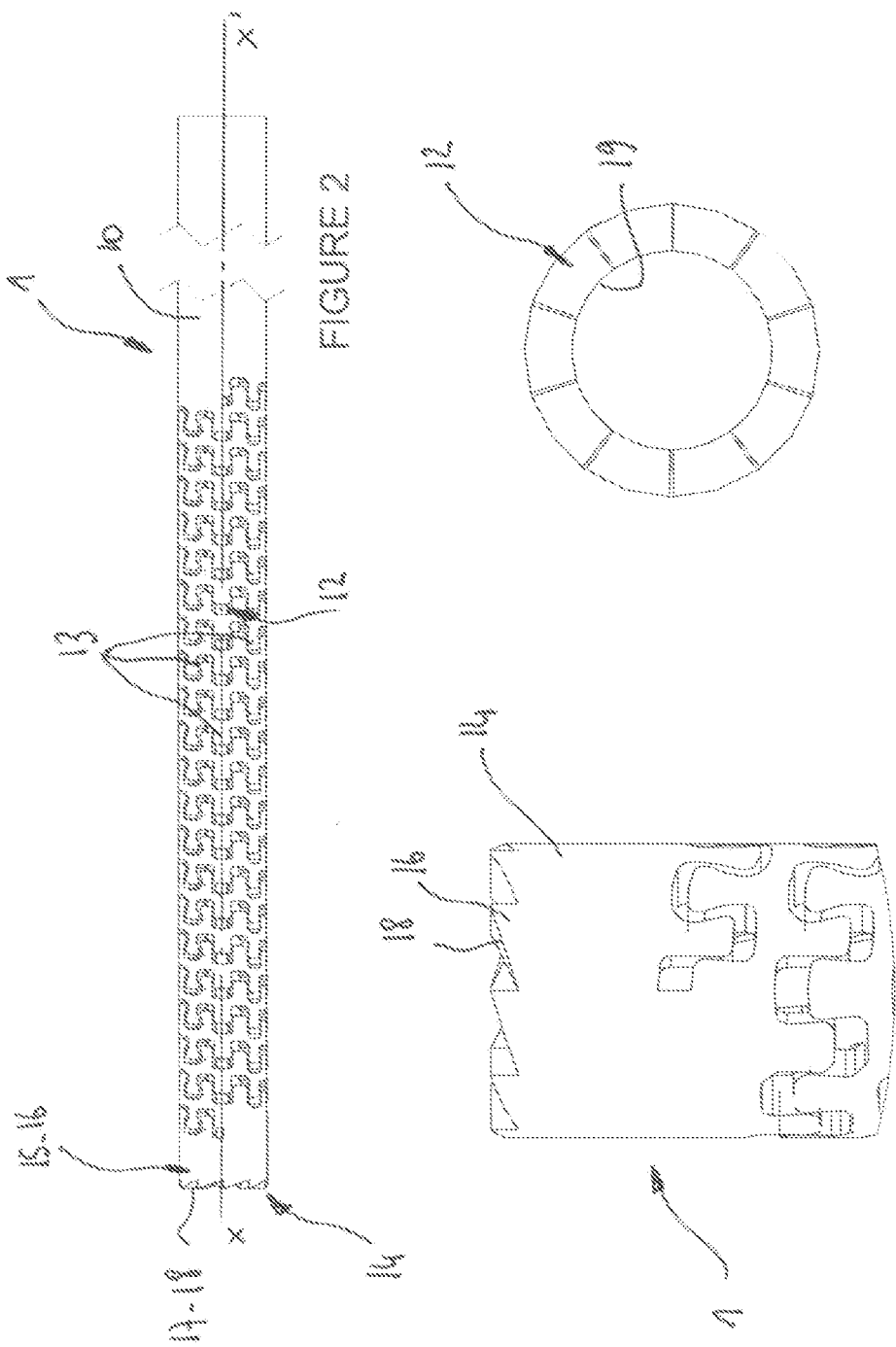

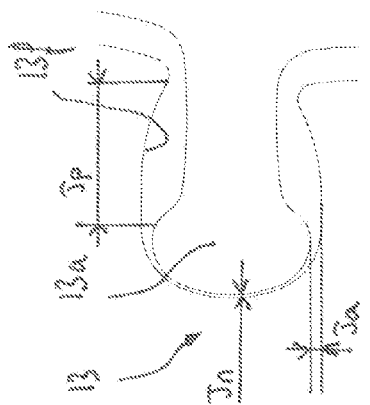
FIGURE 7
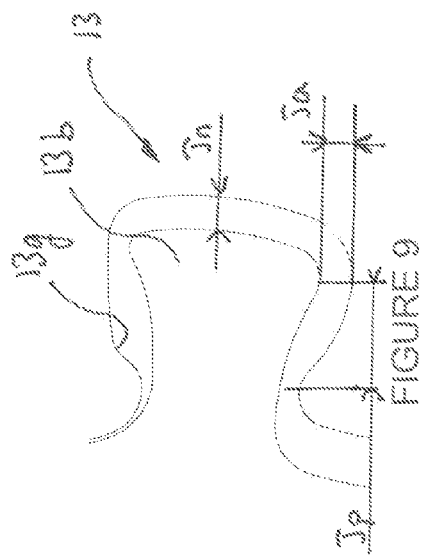
FIGURE 9
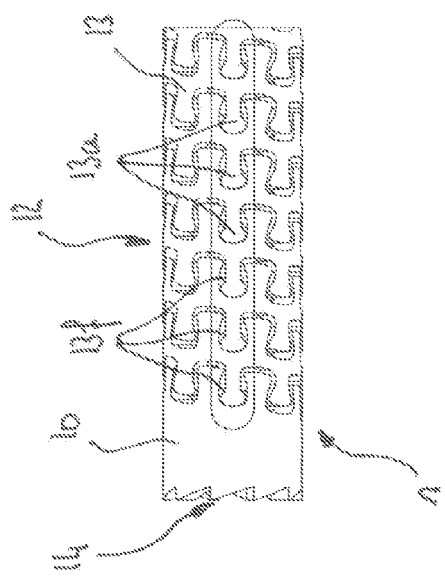
FIGURE 6
FIGURE 8

ARTICULATED DRILL AND DEVICE FOR DRIVING IT IN A RECIPROCATING MOVEMENT

The present invention relates to an articulated drill for carrying out drilling procedures with a small radius of curvature by means of a device for driving the drill in a reciprocating movement.

The patent application FR 11 00199 belonging to the applicant discloses an articulated drill belonging to the applicant, which articulated drill is composed of a metal tube comprising, at one of its ends, an articulated profile formed by concave and convex loops that are obtained through the arrangement of teeth and of seats regularly distributed on the periphery of said tube.

It will be noted that the shape of the teeth and of the seats forming the loops does not allow the articulated profile to curve along a radius of small diameter.

The reason is that, when the profile of the metal tube curves, the play between the teeth inside the radius of curvature decreases, while the play between the teeth outside said radius of curvature increases.

In this situation, if a torque is applied to the metal tube, it will be transmitted only by the teeth inside the radius of curvature. This will have the effect of deforming the articulated profile of the metal tube, since the stress is not distributed across the whole diameter of the different sections constituting the articulated profile but only at a single point. Once the articulated profile is deformed, the teeth can no longer lock together because they are no longer positioned opposite one another, leading to the rupture of the articulated profile of the metal tube.

The object of the present invention is to make available an articulated drill whose articulated profile is capable of deforming along radii of small curvature without risk of unlocking of the teeth when a couple is applied to the metal tube.

The articulated drill according to the present invention is designed in particular for the drilling of channels and of channels of curved profile formed in bone elements, for example in the osseous part of vertebral bodies of a vertebral column.

The articulated drill according to the present invention makes it possible to form channels of curved profile in the vertebral body of the vertebrae in order to reach the intervertebral disc located between the upper and lower vertebrae of a damaged segment of the spine.

The drilling device according to the present invention is composed of an articulated drill provided with a metal tube comprising, along its longitudinal axis XX', and at one of its ends, fixing means that cooperate with a device for driving it in an oscillatory movement, while the other end comprises, on the one hand, a profile with a succession of alternately concave and convex loops ensuring the deformation of said profile along a radius of curvature r, and, on the other hand, at least one series of teeth with cutting edges.

The drilling device according to the present invention is composed of an articulated drill in which the first series of teeth has a cutting edge which is inclined with respect to the longitudinal axis XX' of the metal tube by an angle $\alpha$ of between 5 and 15 degrees.

The drilling device according to the present invention is composed of an articulated drill in which the second series of teeth has a cutting edge which is inclined with respect to the longitudinal axis XX' of the metal tube by an angle $\beta$ of between 55 and 80 degrees.

The drilling device according to the present invention is composed of an articulated drill in which the metal tube has, in its inner part, a protective sheath of flexible material defining an internal bore for internally smoothing the roughnesses and the discontinuities of the free end of the profile formed by the succession of alternately concave and convex loops.

The drilling device according to the present invention is composed of an articulated drill in which the profile of the metal tube is formed by a combination of loops constituted, on the periphery of said metal tube, by teeth cooperating respectively in seats in such a way as to constitute an asymmetrical and alternately concave and convex profile.

The drilling device according to the present invention is composed of an articulated drill in which the profile of the metal tube has, on the external fibre or face Fs of the radius of curvature r, the upper teeth, adjacent teeth, intermediate teeth and lateral teeth, and, on the internal fibre or face Fi, the notched teeth.

The drilling device according to the present invention is composed of an articulated drill in which each loop of the profile has, between the edges of the tooth and the edges of the corresponding seat, a functional play of positive axial displacement Jp, a functional play of negative axial displacement Jn, and a functional play of angulation Ja allowing said profile of the metal tube, on the one hand, to curve progressively without unlocking of the upper tooth and of the adjacent teeth until reaching the radius of curvature r, and, on the other hand, to withstand the stresses of the oscillatory movements.

The drilling device according to the present invention is composed of an articulated drill comprising fixing means that are composed of a cylindrical sleeve cooperating with a bore of complementary shape formed in a cylindrical sleeve free in rotation and guided axially inside a support housing of the drive device.

The drilling device according to the present invention is composed of an articulated drill in which the cylindrical sleeve of the fixing means has a flattened surface provided at its centre with an angular indexing strip cooperating with a groove of the same profile formed in the bore of the support housing.

The drilling device according to the present invention is composed of an articulated drill in which the cylindrical sleeve of the fixing means is provided, at one of its ends, with a peripheral abutment for blocking the engagement in translation of the metal tube inside the bore.

The drilling device according to the present invention is composed of a drive device, of which the support housing has, below the bore and counter to the direction of introduction of the metal tube, means for receiving and fixing an electric motor.

The drilling device according to the present invention comprises a drive device comprising, inside the support housing, transmission means for converting the movement of continuous rotation of the electric motor into an oscillatory or reciprocating movement with an amplitude of at least 60 degrees.

The drilling device according to the present invention is composed of a drive device in which the transmission means are composed of a first toothed wheel integral with the output shaft of the electric motor and meshing with a second toothed wheel of greater dimensions than the first, said second toothed wheel being mounted about a rotation axle which is guided inside the support housing, said second toothed wheel being integral with a first crankshaft cooperating freely in rotation with the first end of a connecting rod, of which the other end is mounted, also freely in rotation, about a second crankshaft integral with the cylindrical sleeve of the bore in order to drive the cylindrical sleeve in an oscillatory movement.

In the following description, which will give a better understanding of the invention, of the features of the invention and of the advantages that the invention is likely to afford, reference is made to the attached drawings, which are given as non-limiting examples and in which:

FIGS. 1 and 1a are views illustrating the articulated drill and the device for driving it in a reciprocating movement, making it possible to carry out drilling procedures with a small radius of curvature according to the present invention.

FIGS. 2 to 4 are views showing in detail the articulated profile of the drill according to the present invention, provided with a cutting end comprising a first and second series of teeth of different inclination.

FIGS. 6 and 7 are views illustrating in detail the shape of the alternately concave and convex loops of the upper teeth of the articulated profile of the drill according to the present invention.

FIGS. 8 and 9 are views showing in detail the shape of the alternately concave and convex loops of the adjacent teeth of the articulated profile of the drill according to the present invention.

Figure 1:
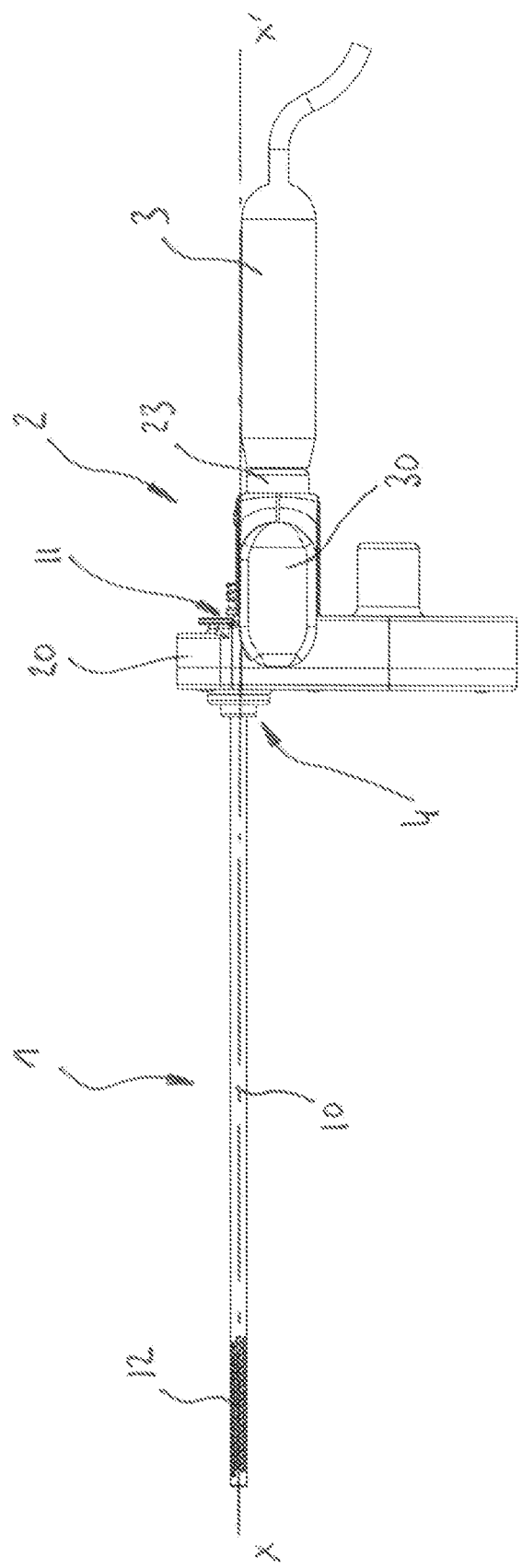

In FIGS. 1 and 1a, an articulated drill 1 has been shown arranged on a device 2 for driving it in a reciprocating movement and ensuring the oscillatory movements of said drill about the longitudinal axis XX' thereof.

The articulated drill 1 is composed of a cylindrical metal tube 10 having, at one of its ends, fixing means 11 that cooperate with a profile of complementary shape formed in the drive device 2, while the other end is cut along a profile 12 that can be formed, for example, by a succession of alternately concave and convex loops 13 ensuring the deformation and the articulation of said end along a curve of radius r.

In FIGS. 2 to 4, 4a and 4b, the metal tube 10 has been shown terminating, after the profile 12, in a cutting end 14 which comprises, for example, a first and second series of teeth 15, 16, each having respective cutting edges 17, 18 of different inclination.

The first series of teeth 15 has a cutting edge 17 which is inclined with respect to the longitudinal axis XX' of the metal tube 10 by an angle α of between 5 and 15 degrees.

The second series of teeth 16 has a cutting edge 18 which is inclined with respect to the longitudinal axis XX' of the metal tube 10 by an angle β of between 55 and 80 degrees.

By way of a non-limiting example, the cutting end 14 can comprise at least one series of teeth with cutting edges.

It will also be noted that the pitch of the tooth is sufficiently small to ensure that, during the reciprocating movement, the displacement of one tooth straddles at least the cut made by the preceding tooth.

Figure 4A:
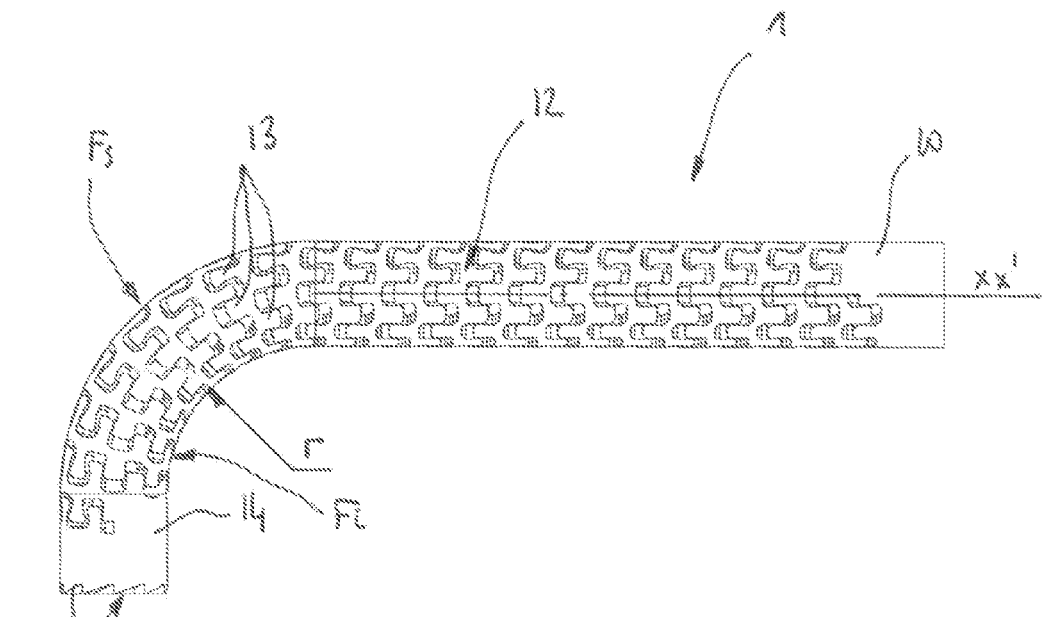
FIGS. 4a and 4b are views illustrating the deformation of the articulated profile along a radius of curvature defined by the drill according to the present invention.
Figure 4B:
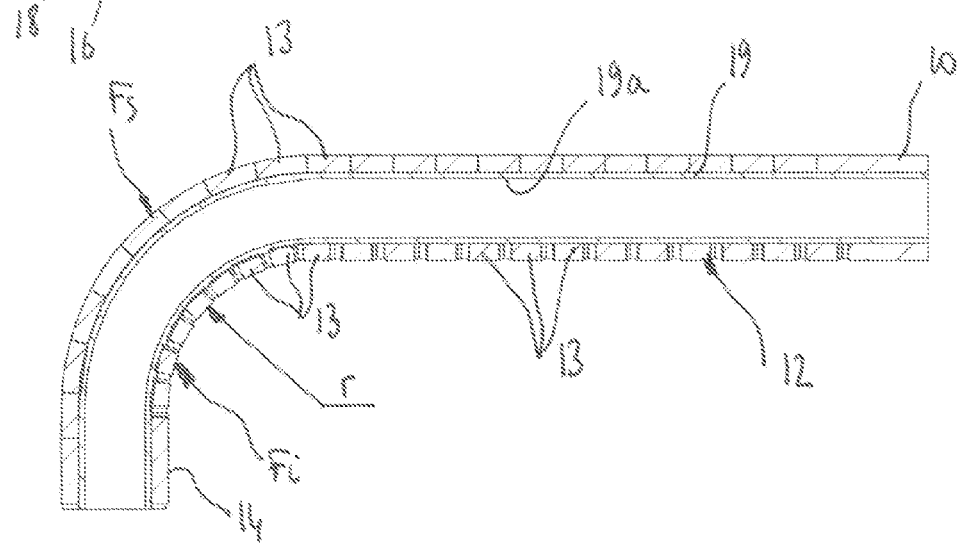

The articulated drill 1 has, in the inner part of the metal tube 10, a protective sheath 19 of flexible material defining an internal bore 19a for internally smoothing the roughnesses and the discontinuities of the free end of the profile 12 formed, for example, by the succession of alternately concave and convex loops 13 (FIGS. 4 and 4b).

The protective sheath 19 can be made, for example, of a flexible material such as PTFE that also ensures a high coefficient of sliding to permit the sliding of a guide element or similar (FIGS. 4 and 4b).

Figure 5:
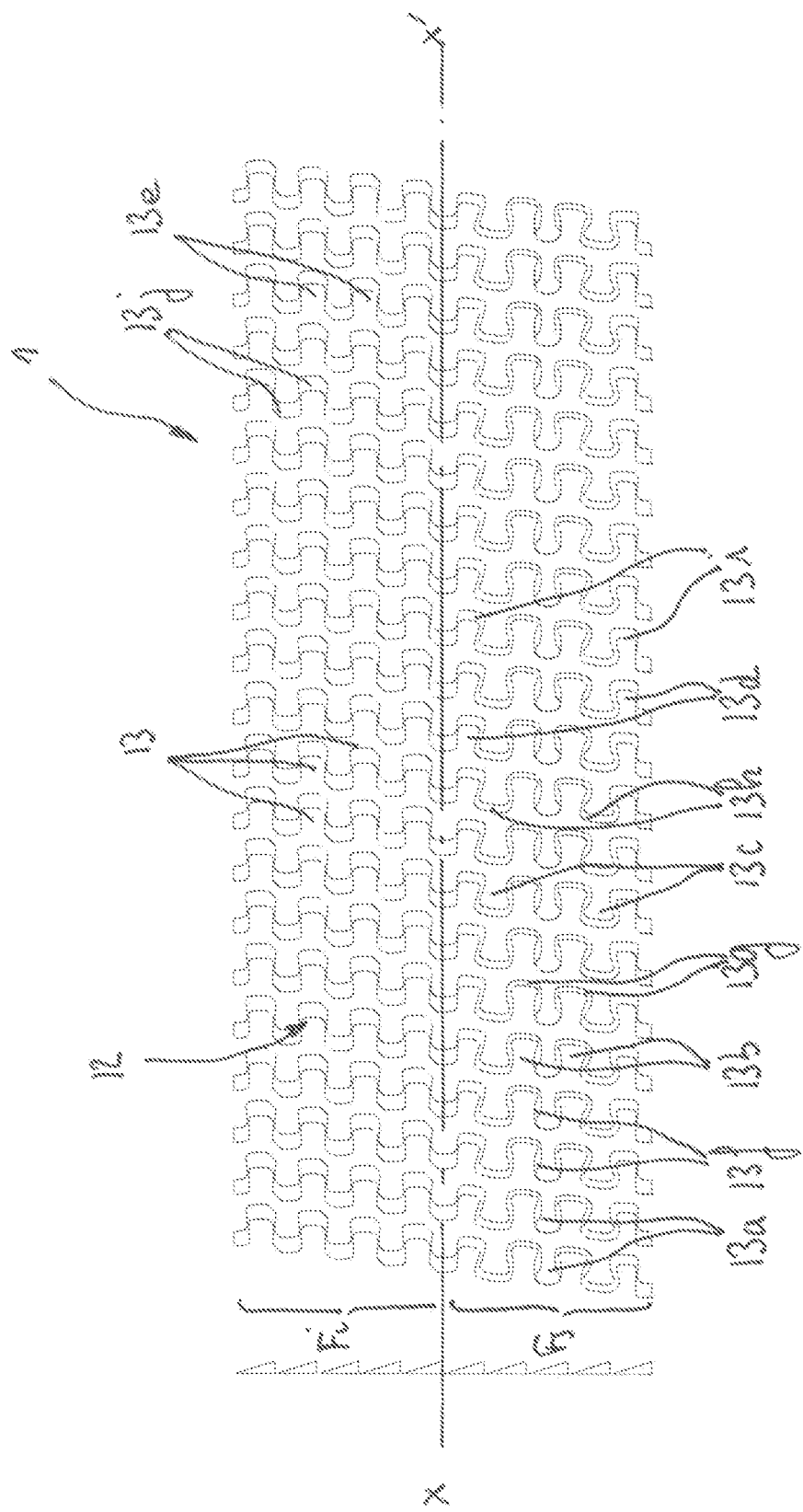
FIG. 5 is an opened-out view showing the shape of each of the alternately concave and convex loops of the articulated profile of the drill according to the present invention.

FIGS. 4a and 5 illustrate the profile 12 of the articulated drill 1 which is formed, for example, by a combination of loops 13 constituted, on the periphery of the metal tube 10, by teeth 13a to 13e cooperating respectively in seats 13f to 13j in such a way as to constitute an asymmetrical and alternately concave and convex profile.

Depending on the desired radius of curvature r of the articulated drill 1, the profile 12 comprises, on the one hand on the periphery of the metal tube 10, a number of loops 13 of between six and eight and, on the other hand between the cutting end 14 and the start of said profile 12, a number of revolutions of between fifteen and twenty five.

According to a preferred embodiment of the invention, the articulated drill 1 has a profile 12 which is formed, on the periphery of the metal tube 10, by at least seven loops 13 arranged on the external fibre or face Fs and by at least seven other loops 13 on the internal fibre or face Fi when said profile 12 is deformed with respect to the axis XX' along the radius of curvature r (FIG. 4a).

Moreover, according to a preferred embodiment of the invention, the articulated drill has a profile 12 comprising, between the cutting end 14 and the start of said profile 12, a number of twenty and an asymmetrical revolution of loops 13.

The asymmetrical cut of the loops 13 makes it possible to adapt the shape of each tooth 13a to 13e depending on its position on the metal tube 10. The length of the upper tooth 13a is in fact adapted such that the couple is transmitted by all the teeth 13b to 13e located on the periphery of the metal tube 10.

Moreover, through the combination of the length of the upper tooth 13a, the diameter of the metal tube 10 and the functional play Ja, Jp, Jn of each tooth, it is possible to define the maximum radius of curvature r of the profile 12.

Thus, when the profile 12 of the metal tube 10 is in a straight and undeformed position, there is a very small functional play of the teeth 13a to 13d located on the external fibre or face Fs and a greater functional play on the teeth 13e arranged on the internal fibre or face Fi. By contrast, when the profile 12 of the metal tube is deformed along the radius of curvature r, the shape of the teeth 13a to 13e means that there is considerable functional play in the area of the external fibre or face Fs and a small functional play in the area of the internal fibre Fi.

For example, the profile 12 of the articulated drill 1 comprises, on the external fibre or face Fs, seven asymmetrical loops 13 constituting:
- an upper tooth 13a,
- two adjacent teeth 13b,
- two intermediate teeth 13c,
- two lateral teeth 13d.

Moreover, for example, the profile 12 of the articulated drill 1 comprises, on the internal fibre or face Fi, seven asymmetrical loops 13 constituting:
- seven notched teeth 13e.

On account of this particular arrangement of the asymmetrical loops 13 on the periphery of the metal tube 10 and more particularly in the area of the external fibre or face Fs and internal fibre or face Fi, the articulated drill 1 can be driven by the drive device 2 in a reciprocating rotation movement that can be of more or less 60 degrees, i.e. an amplitude of 120 degrees.

The profile of each tooth 13a to 13e has a functional play increasing between the longitudinal axis of the cylindrical tube 10 and the internal fibre or face Fi of the radius of curvature r, favouring the inter-meshing of the loops 13 during a deformation of the profile 12 and more particularly during a deformation, along a radius of curvature r, of between five and fifteen millimeters.

It is in fact imperative, during this deformation of the profile 12 and during the driving of the metal tube 10 in a reciprocating rotation movement, that the teeth 13a to 13e are always in mutual contact without risk of coming loose or unlocking.

For this purpose, each loop 13 has, between the edges of the tooth 13a to 13e and the edges of the corresponding seat 13f to 13j, a functional play of positive axial displacement Jp, a functional play of negative axial displacement Jn, and a functional play of angulation Ja.

The functional plays of positive axial displacement Jp and of negative axial displacement Jn and the functional play of angulation Ja allow the profile 12 of the metal tube 10, on the one hand, to curve progressively until reaching the radius of curvature r of functioning and drilling, and, on the other hand, to withstand the stresses of the reciprocating movements.

FIGS. 6 and 7 show a series of loops 13 constituting, along the length of the profile 12, teeth 13a called "upper teeth" of concave profile cooperating in seats 13f of complementary convex shape.

Each upper tooth 13a has a concave profile oriented in the direction of the cutting end 14 of the metal tube 10, while the seat 13f is oriented in an opposite direction.

Of the set of teeth 13a to 13e constituting the profile 12, the upper tooth 13a is the one with the greatest play of positive axial displacement Jp, of about $75/100$ to $80/100$ of a millimeter, on account of its position on the periphery of the metal tube 10. This is because the upper teeth 13a are all located on the external fibre or face Fs of the radius of curvature r.

For this purpose, the more the profile 12 of the metal tube 10 curves, the more the play of positive axial displacement Jp decreases until it reaches the maximum curvature of said radius of curvature r and a play of positive axial displacement Jp of almost zero.

By contrast, each upper tooth 13a has, with its seat 13f, a functional play of negative axial displacement Jn of about $2/100$ to $4/100$ of a millimeter, since the latter, because of its position, never works in compression. This functional play of negative axial displacement Jn is the weakest in relation to those applied to the other teeth.

The functional play of angulation Ja is about $5/100$ to $8/100$ of a millimeter, since each upper tooth 13a has no need to pivot in its seat 13f. The reason is that, in the extreme position of the reciprocating rotary movement, each upper tooth 13a is never situated in an unfavourable position because of its axial positioning during the deformation of the profile 12 of the metal tube 10.

Each upper tooth 13a has the function of transmitting the couple issuing from the reciprocating rotary movement of the drive device 2 allowing the articulated drill 1 to drill the channel of curved profile.

During the deformation of the profile 12 and the driving of the metal tube 10 in reciprocating rotation, the profile of each upper tooth 13a and the profile of each seat 13f avoid the unlocking of said teeth and the risk of rupturing of the articulated drill 1.

FIGS. 8 and 9 show a series of loops 13 constituting, along the length of the profile 12, teeth 13b called "adjacent teeth" of concave profile cooperating in seats 13g of complementary convex shape.

The adjacent teeth 13b and the seats 13g are situated in the continuation of and on either side of the upper teeth 13a of the profile 12.

The adjacent teeth 13b and the seats 13g are oriented respectively in a direction counter to that of the upper teeth 13a and of the seats 13f.

Each adjacent tooth 13b has, with its seat 13g, a play of positive axial displacement Jp similar to that of the upper teeth 13a, of about $75/100$ to $80/100$ of a millimeter, on account of its position on the periphery of the metal tube 10. This is because the adjacent teeth 13b are all located on the external fibre or face Fs of the radius of curvature r.

Each adjacent tooth 13b has, with its seat 13g, a functional play of negative axial displacement Jn of about $15/100$ to $25/100$ of a millimeter in order to ensure compression work of each of said adjacent teeth 13b.

Each adjacent tooth 13b has, with its seat 13g, a play of angulation Ja of between $10/100$ and $12/100$ of a millimeter, ensuring the rotation of the tooth in its seat when it reaches, in the extreme position, a substantial angulation.

Each adjacent tooth 13b has the function of transmitting the couple issuing from the reciprocating rotary movement of the drive device 2 allowing the articulated drill 1 to drill the channel of curved profile.

During the deformation of the profile 12 and the driving of the metal tube 10 in reciprocating rotation, the profile of each adjacent tooth 13b and the profile of each seat 13g avoid the unlocking of said teeth and the risk of rupturing of the articulated drill 1.

Figures 10, 11, 12, 13:
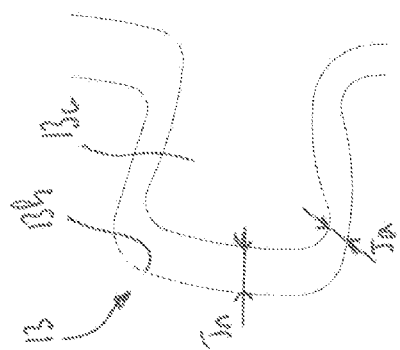
FIGS. 10 and 11 are views showing in detail the shape of the alternately concave and convex loops of the intermediate teeth of the articulated profile of the drill according to the present invention.
FIGS. 12 and 13 are views showing in detail the shape of the alternately concave and convex loops of the lateral teeth of the articulated profile of the drill according to the present invention.

FIGS. 10 and 11 illustrate a series of loops 13 constituting, along the length of the profile 12, teeth 13c called "intermediate teeth" of concave profile cooperating in seats 13h of complementary convex shape.

The intermediate teeth 13c and the seats 13h are situated in the continuation of and on either side of the adjacent teeth 13b and corresponding seats 13g of the profile 12.

The intermediate teeth 13c and the seats 13h are oriented respectively in the same direction as that of the upper teeth 13a and of the seats 13f, that is to say in the direction of the cutting end 14 as regards said intermediate teeth 13c.

Each intermediate tooth 13c has, with its seat 13h, an infinite play of positive axial displacement Jp allowing it to leave the seat on account of its position on the periphery of the metal tube 10. This is because the intermediate teeth 13c are all located on the external fibre or face Fs of the radius of curvature r.

Each intermediate tooth 13c has, with its seat 13h, a functional play of negative axial displacement Jn of about $15/100$ to $35/100$ of a millimeter in order to ensure compression work of each of said teeth.

Each intermediate tooth 13c has, with its seat 13h, a play of angulation Ja of between $10/100$ and $15/100$ of a millimeter, ensuring the inclination of the tooth in its seat when it reaches, in the extreme position, a substantial angulation.

Each intermediate tooth 13c has the function of transmitting the couple issuing from the reciprocating rotary movement of the drive device 2 allowing the articulated drill 1 to drill the channel of curved profile.

Moreover, each intermediate tooth 13c, because of its profile, determines the amplitude of the metal tube 10 and of the profile 12 and ensures the safety of the other teeth in the extreme position, since it serves as abutment.

FIGS. 12 and 13 show a series of loops 13 constituting, along the length of the profile 12, teeth 13d called "lateral teeth" of concave profile cooperating in seats 13i of complementary convex shape.

The lateral teeth 13d and the seats 13i are situated in the continuation of and on either side of the intermediate teeth 13c and corresponding seats 13h of the profile 12.

Each lateral tooth 13d has, with its seat 13i, an infinite play of positive axial displacement Jp allowing it to leave the seat on account of the small length of said tooth and its position on the periphery of the metal tube 10.

This is because the lateral teeth 13d are all located on the external fibre or face Fs of the radius of curvature r.

Each lateral tooth 13d has, with its seat 13i, a functional play of negative axial displacement Jn of about $25/100$ to $45/100$ of a millimeter in order to ensure the desired curvature of the profile 12 in the extreme position.

Each lateral tooth 13d has, with its seat 13i, a small play of angulation Ja of between $2/100$ and $8/100$ of a millimeter, ensuring in combination with its small length the inclination and pivoting of said tooth in its seat.

Each lateral tooth 13d has the function of transmitting the couple issuing from the reciprocating rotary movement of the drive device 2 allowing the articulated drill 1 to drill the channel of curved profile.

Figure 15:
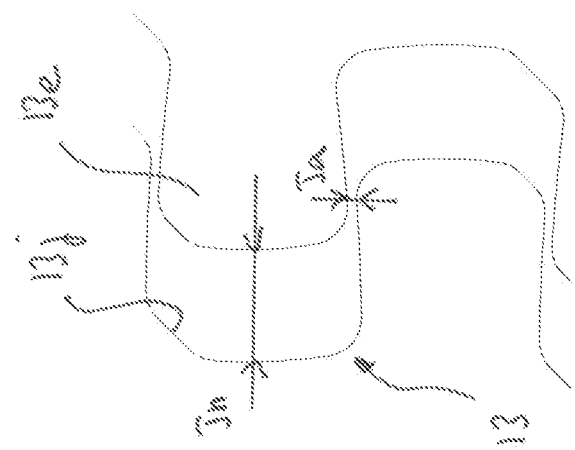
FIGS. 14 and 15 are views illustrating in detail the shape of the alternately concave and convex loops of the notched teeth of the articulated profile of the drill according to the present invention.
Figure 14:
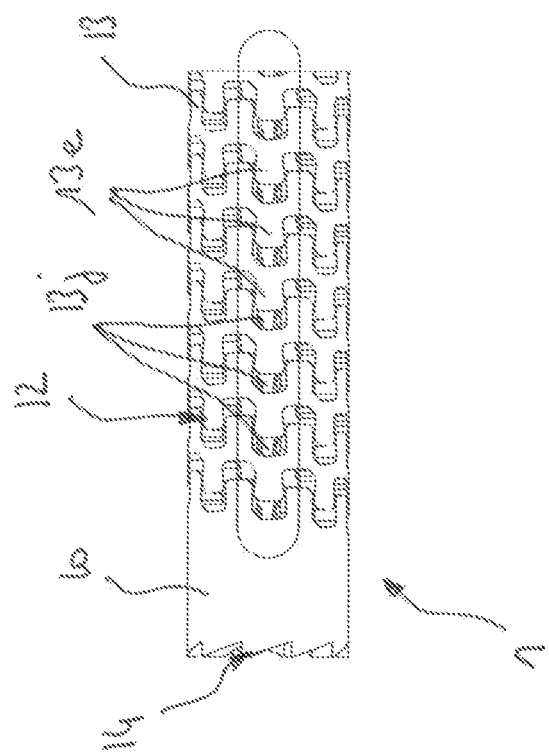
Figure 16:
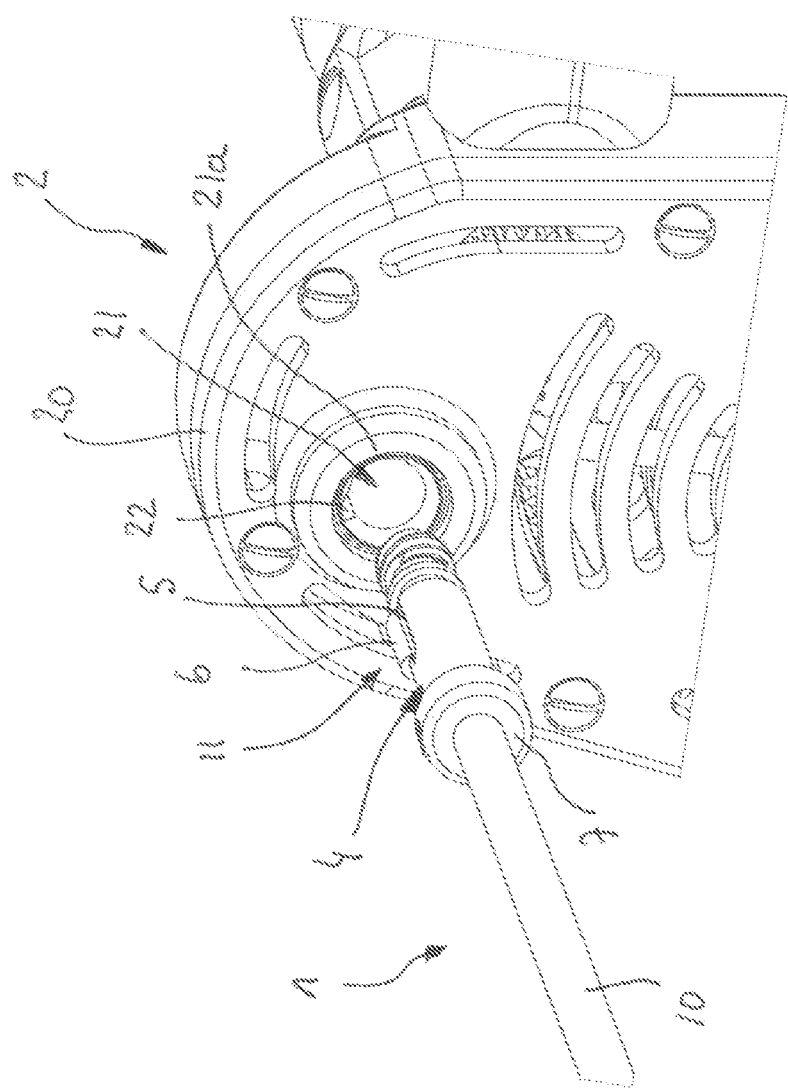
FIG. 16 is an exploded perspective view showing the means of coupling the articulated drill in the device for driving it in a reciprocating movement according to the present invention.
Figure 17:
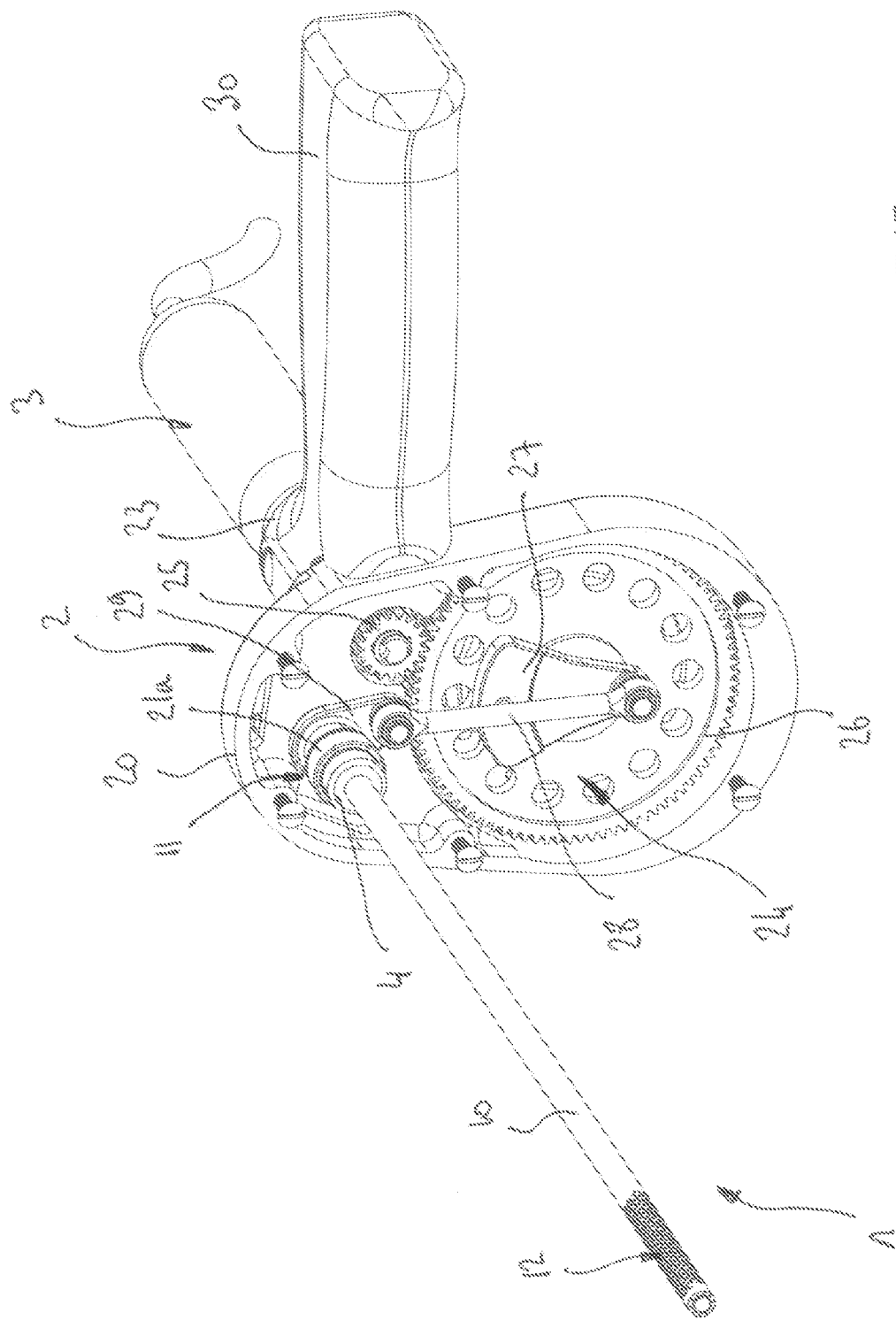
FIG. 17 is a perspective view showing the drive means of the device for driving in a reciprocating movement according to the present invention.

FIGS. 14 and 15 illustrate a series of loops 13 constituting, along the length of the profile 12, teeth 13e called "notched teeth" with a concave profile cooperating in seats 13j of complementary convex shape.

The notched teeth 13e and the seats 13j are situated in the continuation of and on either side of the lateral teeth 13d and corresponding seats 13i of the profile 12, so as to be located on the internal face or fibre Fi of the radius of curvature r of the profile 12.

Each notched tooth 13e has, with its seat 13j, an infinite play of positive axial displacement Jp allowing it to leave the seat on account of the small length of said tooth and its position on the periphery of the metal tube 10.

Each notched tooth 13e has, with its seat 13j, a functional play of negative axial displacement Jn of about $70/100$ to $80/100$ of a millimeter in order to ensure the desired curvature of the profile 12 in the extreme position.

The length of each notched tooth 13e is determined in such a way that it has the greatest functional play of negative axial displacement Jn while maintaining the meshing of said teeth when the profile 12 of the metal tube 10 is in the straight position, that is to say not curved.

Each notched tooth 13e has, with its seat 13j, a small play of angulation Ja of between $2/100$ and $8/100$ of a millimeter, ensuring in combination with its small length the inclination and pivoting of said tooth in its seat.

The small play of angulation Ja of each notched tooth 13e makes it possible to avoid loss of amplitude, that is to say it participates in recovering the functional plays during the motorization of the articulated drill 1 in a reciprocating rotary movement.

Each notched tooth 13e has the function of transmitting the couple issuing from the reciprocating rotary movement of the drive device 2 allowing the articulated drill 1 to drill the channel of curved profile.

It will be noted that the particular profile of each of the upper 13a, adjacent 13b, intermediate 13c, lateral 13d and notched 13e teeth of the profile 12 makes it possible to transmit all of the couple in the straight or curved position of the articulated drill 1 during the drilling of the channel.

FIGS. 1, 1a, 16 and 17 illustrate the device 2 for driving in a reciprocating movement, ensuring the oscillatory movements of the articulated drill 1 about its longitudinal axis XX'.

The articulated drill 1 is always arranged in the same axial position on the drive device 2 in such a way as to position the profile 12 always in the same position of curvature, such that the teeth 13a to 13d are located on the external fibre or face Fs of the radius of curvature r and the notched teeth 13e are arranged on the internal fibre or face Fi of said radius of curvature r.

For this purpose, the articulated drill 1 comprises, opposite the cutting end 14, an end integrally connected to fixing means 11 cooperating with a bore 21 of complementary shape formed in a cylindrical sleeve 21a free in rotation and guided axially inside the support housing 20 of the drive device 2.

The fixing means 11 are composed of a cylindrical sleeve 4 having, on its outer face, a flattened surface 5 provided at its centre with an angular indexing strip 6 cooperating with a groove 22 of the same profile formed in the bore 21 of the support housing 20. The cylindrical sleeve 4 is provided, at one of its ends, with a peripheral abutment 7 for blocking the engagement in translation of the articulated drill 1 inside the bore 21.

The support housing 20 of the drive device 2 has, below the bore 21 and counter to the direction of introduction of the articulated drill 1, means 23 for receiving and fixing an electric motor 3.

The drive device 2 comprises, inside the support housing 20, transmission means 24 for converting the movement of continuous rotation of the electric motor 3 into an oscillatory or reciprocating movement with an amplitude of about 120 degrees.

The transmission means 24 are composed of a first toothed wheel 25 integral with the output shaft of the electric motor 3 and meshing with a second toothed wheel 26 of greater dimensions than the first.

The second toothed wheel 26 is mounted about a rotation axle which is guided inside the support housing 20.

The second toothed wheel 26 is integral with a first crankshaft 27 cooperating freely in rotation with the first end of a connecting rod 28, of which the other end is mounted, also freely in rotation, about a second crankshaft 29 integral with the cylindrical sleeve 21a of the bore 21 in order to drive the cylindrical sleeve in an oscillatory movement.

The functioning of the drive device 2 will be easily understood from the above description, namely that when the articulated drill 1 is engaged in the bore 21 of the support housing 20, it can be driven by the drive device 2 in an oscillatory movement with an amplitude of about 120 degrees.

In the area of the receiving means 23 and in a direction perpendicular thereto, the drive device 2 comprises a handle 30 permitting manipulation of said device integral with the articulated drill 1.

It must also be appreciated that the above description has been given solely by way of example and does not in any way limit the scope of the invention, and replacing the described embodiments by any other equivalent embodiments would not represent a departure from the scope of the invention.

The invention claimed is:

1. A drilling device for forming a channel of curved profile, the device comprising:

an articulated drill comprising a tube with one end adapted to be attached to a device for driving the drill in an oscillatory movement and a second end with a series of teeth with cutting edges, the tube having between the two ends a profile deformable along a radius of curvature r, the profile comprising a succession of alternately concave and convex loops that form teeth and cooperating seats arranged on an exterior face of the profile and on an interior face of the profile with respect to an axis of the profile when the profile is deformed along the radius of curvature r, and wherein between edges of adjacent teeth and between edges of the teeth and cooperating seats are a functional play of positive axial displacement Jp, a functional play of negative axial displacement Jn, and a functional play of angulation Ja, wherein the teeth on the exterior face comprise upper teeth most remote from the interior face and adjacent teeth that are directly adjacent opposite edges of a respective upper tooth, and wherein the teeth on the interior face comprise plural notched teeth, and wherein the functional play of negative axial displacement Jn for the upper teeth is less than that of the adjacent teeth, and wherein the functional play of positive axial displacement Jp for the upper teeth is less than that of the plural notched teeth.

2. The drilling device according to claim 1, wherein the functional play of angulation Ja of the upper teeth is less than that of the adjacent teeth.

3. The drilling device according to claim 1, wherein the teeth on the exterior face further comprise intermediate teeth that are directly adjacent edges of respective adjacent teeth, and lateral teeth that are directly adjacent edges of respective intermediate teeth, and wherein the functional plays of positive displacement for the upper and adjacent teeth are each less than that of the intermediate and lateral teeth, and wherein the functional plays of negative displacement for the upper, adjacent, intermediate, and lateral teeth are each less than that of the notched teeth.

4. The drilling device according to claim 3, wherein the functional plays of positive displacement for the upper and adjacent teeth are $^{75}/_{100}$ to $^{80}/_{100}$ of a millimeter and those of the intermediate, lateral and notched teeth are infinite.

* * * * *